US00PP08782P

United States Patent [19]

Fuess

[11] Patent Number: Plant 8,782

[45] Date of Patent: Jun. 14, 1994

[54] CHRYSANTHEMUM PLANT NAMED EMPIRE SYMPHONY

[76] Inventor: Janet S. Fuess, 22 Country Club Dr., New York Mills, N.Y. 13417

[21] Appl. No.: 447

[22] Filed: Jan. 4, 1993

[51] Int. Cl.[5] ..... A01H 5/00
[52] U.S. Cl. ..... Plt./76
[58] Field of Search ..... Plt. 76

*Primary Examiner*—Howard J. Locker
*Attorney, Agent, or Firm*—Foley & Lardner

[57] ABSTRACT

A Chrysanthemum plant named Empire Symphony particularly characterized by its flat capitulum form; decorative capitulum type; purple ray floret color; diameter across face of capitulum of 57 to 64 mm when fully opened; branching pattern is spreading and prolific, with 8 to 10 breaks after pinch when grown outside under natural daylength in fall flowering; natural season flower date of August 27 when planting rooted cuttings on Jun. 25, 1992 in Salinas, Calif., and of September 19 to 21 when planting rooted cuttings June 15 to June 18 in Hightstown, N.J. in 1990 and 1991; not recommended for no light/no shade programs in spring; plant height of 41 to 43 cm when grown in fall under natural daylength with no growth regulators; and durable, uniform performance.

3 Drawing Sheets

The present invention comprises a new and distinct cultivar of Chrysanthemum, botanically known as *Dendranthema grandiflora,* and referred to by the cultivar name Empire Symphony.

Empire Symphony, identified as 8444 (F88-8), was originated from a cross made by Janet S. Fuess in a controlled breeding program in New Hartford, N.Y. in October 1987.

The female parent of Empire Symphony was the cultivar identified as Debonair, disclosed in U.S. Plant Pat. No. 5,324, and described as a purple decorative garden mum.

The male parent of Empire Symphony was an unnamed seedling, identified as B87-53, and described as a deep pink decorative garden mum.

Empire Symphony was discovered and selected as one flowering plant within the progeny of the stated cross by Janet S. Fuess in August 1988 in New Hartford, N.Y.

The first act of asexual reproduction of Empire Symphony was accomplished when vegetative cuttings were taken from the initial selection in October 1988 in a controlled environment in New Hartford, N.Y. by Janet S. Fuess.

Horticultural examination of controlled flowerings of successive plantings has shown that the unique combination of characteristics as herein disclosed for Empire Symphony are firmly fixed and are retained through successive generations of asexual reproduction.

Empire Symphony has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Empire Symphony, which, in combination, distinguish this Chrysanthemum as a new and distinct cultivar:

1. Flat capitulum form.
2. Decorative capitulum type.
3. Purple ray floret color.
4. Diameter across face of capitulum of 57 to 64 mm when fully opened.
5. Branching pattern is spreading and prolific, with 8 to 10 breaks after pinch when grown outside under natural daylength in fall flowerings.
6. Natural season flower date of August 27 when planting rooted cuttings on Jun. 25, 1992 in Salinas, Calif., and of September 19 to 21 when planting rooted cuttings June 15 to June 18 in Hightstown, N.J. in 1990 and 1991.
7. Not recommended for no light/no shade programs in spring.
8. Plant height of 41 to 43 cm when grown in fall under natural daylength with no growth regulators.
9. Durable, uniform performance.

The accompanying photographic drawings show typical inflorescence and leaf characteristics of Empire Symphony, with the colors being as nearly true as possible with illustrations of this type.

Sheet 1 is a color photograph of Empire Symphony grown in natural season outside conditions in Salinas, Calif.

Sheet 2 is a black and white photograph of three views of the inflorescence of Empire Symphony.

Sheet 3 is a black and white photograph showing the under and under sides of the leaves of Empire Symphony at 3 stages of development (mature, intermediate and immature). In sheets 2 and 3 a measuring tape in centimeters has been added.

Of the commercial cultivars known to the inventor, the most similar in comparison to Empire Symphony is the cultivar identified as Debonair, disclosed in U.S. Plant Pat. No. 5,324. Reference is made to attached Chart A, which compares certain characteristics of Empire Symphony to the same characteristics of Debonair.

Similar traits are ray floret color and capitulum form and type. Empire Symphony has a slightly smaller diameter of capitulum, a more prolific branching pattern and a taller plant height when compared with Debonair. In addition, Empire Symphony is not recommended for no light/no shade spring programs, while Debonair is recommended for these programs.

In the following description color references are made to The Royal Horticultural Society Colour Chart. The color values were determined on plant material grown as a pinched garden mum grown outdoors in Salinas, Calif. on Aug. 17, 1992.

Classification:

*Botanical.*—*Dendranthema grandiflora* cv Empire Symphony.

*Commercial.*—Flat decorative garden mum.

I. INFLORESCENCE

A. Capitulum:

*Form.*—Flat.

*Type.*—Decorative.

*Diameter across face.*—57 to 64 mm when fully opened.

B. Corolla of ray florets:

*Color (general tonality from a distance of three meters).*—Purple.

*Color (upper surface).*—71B, fading to 78B.

*Color (under surface).*—77D, tinged with 78B.

*Shape.*—Outer ray florets are spooned, with spoon length approximately 25% of the total ray floret length. Inner ray florets are also spooned, with larger portion of the ray floret being spooned.

C. Corolla of disc florets:

*Color (mature).*—6B.

*Color (immature).*—6B tinged with 151D.

D. Reproductive organs:

*Androecium.*—Present on disc florets only; scant pollen.

*Gynoecium.*—Present on both ray and disc florets.

II PLANT

A. General appearance:

*Height.*—41 to 43 cm when grown in fall under natural daylength with no growth regulators.

*Branching pattern.*—Spreading and prolific, with 8 to 10 breaks after pinch when grown outside under natural daylength in fall flowerings, compared to 5–8 breaks for Debonair when grown under the same conditions.

B. Foliage:

*Color (upper surface).*—147A.

*Color (under surface).*—147B.

*Shape.*—See photograph.

CHART A

COMPARISONS MADE OF PLANTS GROWN AS UNDER NATURAL SEASON OUTDOOR CONDITIONS IN SALINAS, CALIFORNIA AND IN HIGHSTOWN, NEW JERSEY

| CULTIVAR | Empire SYMPHONY | DEBONAIR |
|---|---|---|
| Ray floret color | Purple (7813, mature) | Purple (780, mature) |
| Capitulum form and type | Flat Decorative | Flat Decorative |
| Diameter across face of capitulum | 57 to 64 mm | 64 to 70 mm |
| Branching pattern | Spreading and prolific (8–10 laterals) | Spreading (5–8 laterals) |
| Nat. season flower date: | | |
| in Salinas, CA | Aug 27 | Aug 26 to 31 |
| In Highstown, NJ | Sep 19 to 21 | Sep 24 to 30 |
| Plant height: | | |
| in natural season fall | 41 to 43 cm | 30 to 38 cm |

I claim:

1. A new and distinct Chrysanthemum plant named Empire Symphony, as described and illustrated.

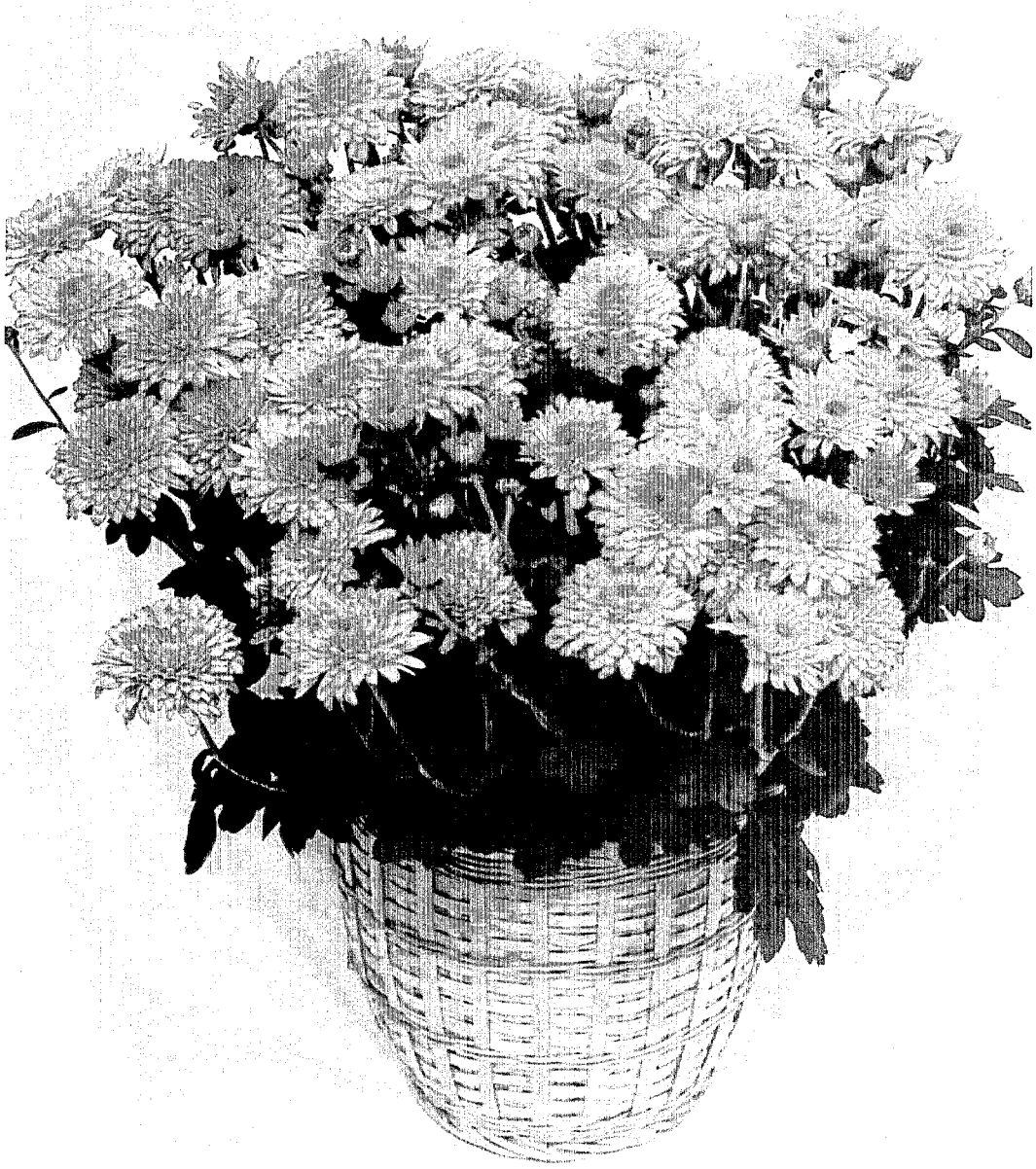

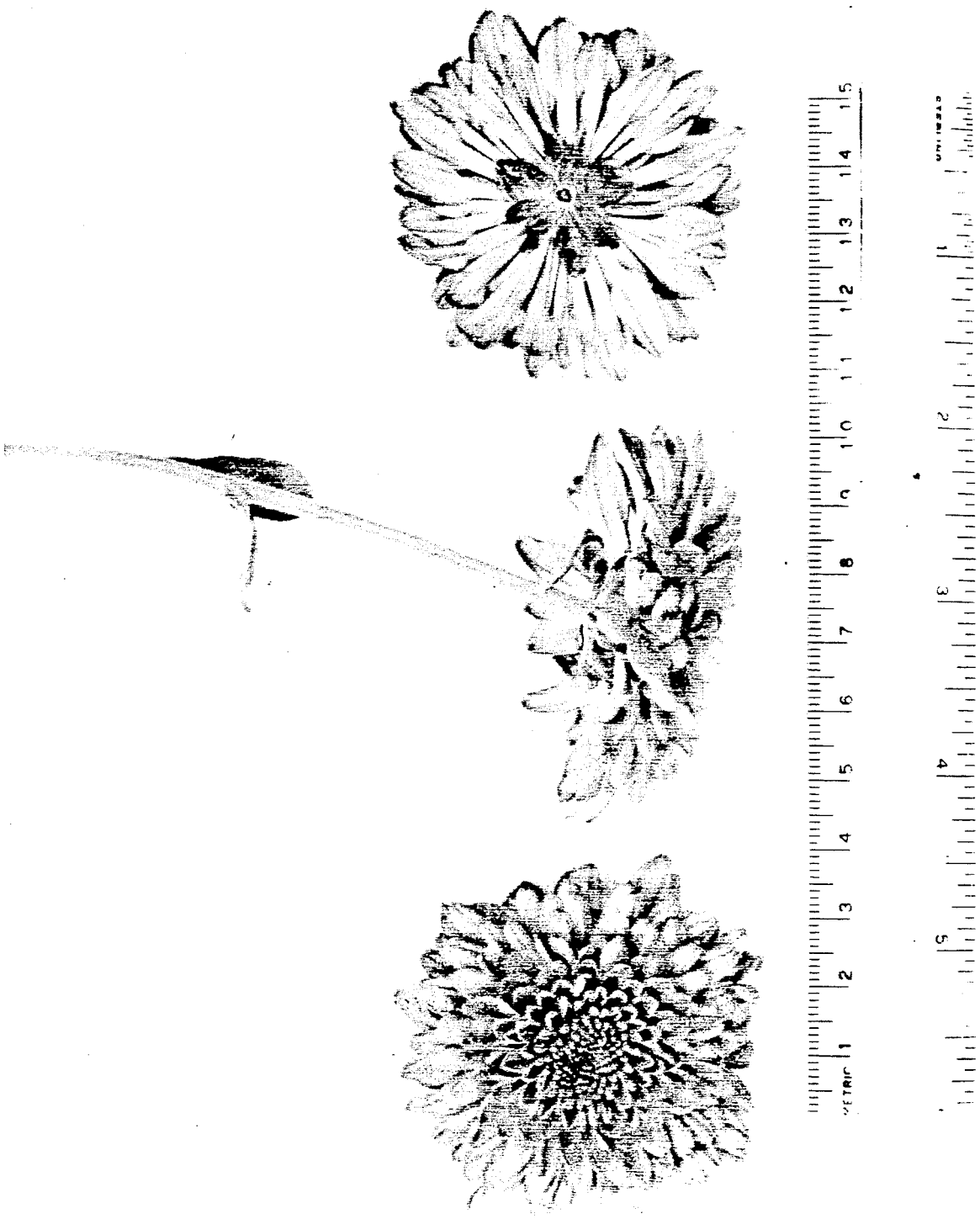

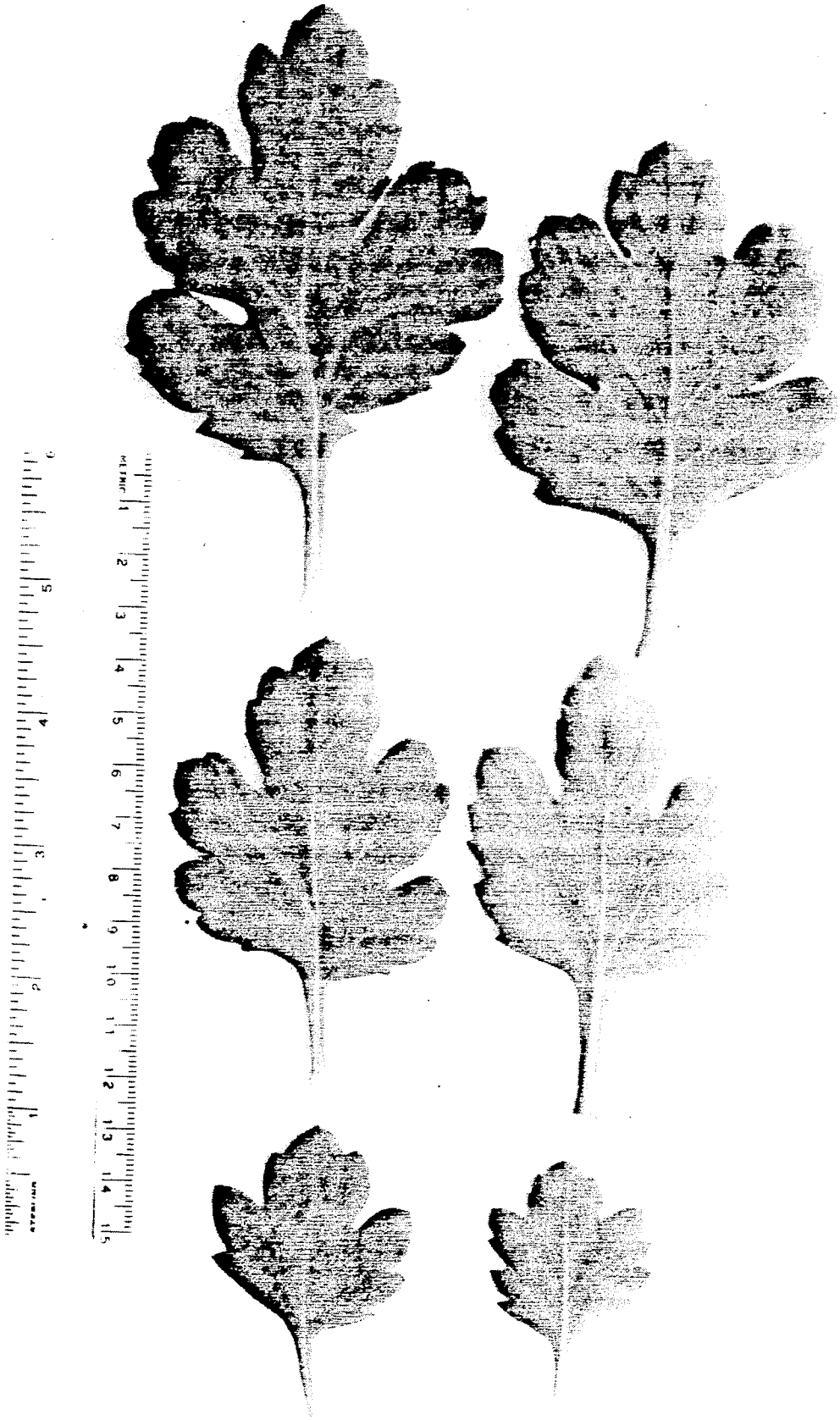

* * * * *